United States Patent [19]

Chien et al.

[11] Patent Number: 5,045,319
[45] Date of Patent: Sep. 3, 1991

[54] TRANSDERMAL DOSAGE UNIT, SYSTEM AND PROCESS

[75] Inventors: Yie W. Chien, North Brunswick; Michael Corbo, Piscataway, both of N.J.

[73] Assignee: Rutgers, The State University of New Jersey, New Brunswick, N.J.

[21] Appl. No.: 259,352

[22] Filed: Oct. 18, 1988

Related U.S. Application Data

[63] Continuation-in-part of Ser. No. 705,194, Feb. 25, 1985, abandoned.

[51] Int. Cl.5 ............................................. A61F 13/02
[52] U.S. Cl. .................................. 424/448; 424/449; 424/447
[58] Field of Search ..................... 424/447, 448, 449

[56] References Cited

U.S. PATENT DOCUMENTS

4,746,515 5/1988 Gale et al. .......................... 424/448
4,769,028 9/1988 Hoffmann et al. .................. 424/447
4,788,062 11/1988 Gale et al. .......................... 424/449

Primary Examiner—Merrell C. Cashion, Jr.
Assistant Examiner—Leon R. Horne
Attorney, Agent, or Firm—Leroy G. Sinn

[57] ABSTRACT

Provided by this invention are novel transdermal dosage units for administering cardiovascular pharmaceuticals, whereby enhanced absorption with essentially zero-order kinetics is obtained. Also provided is a process for administration of cardiovascular pharmaceuticals by use of said dosage units.

2 Claims, 7 Drawing Sheets

FIG. 2

FIG. 3

Figure 1:
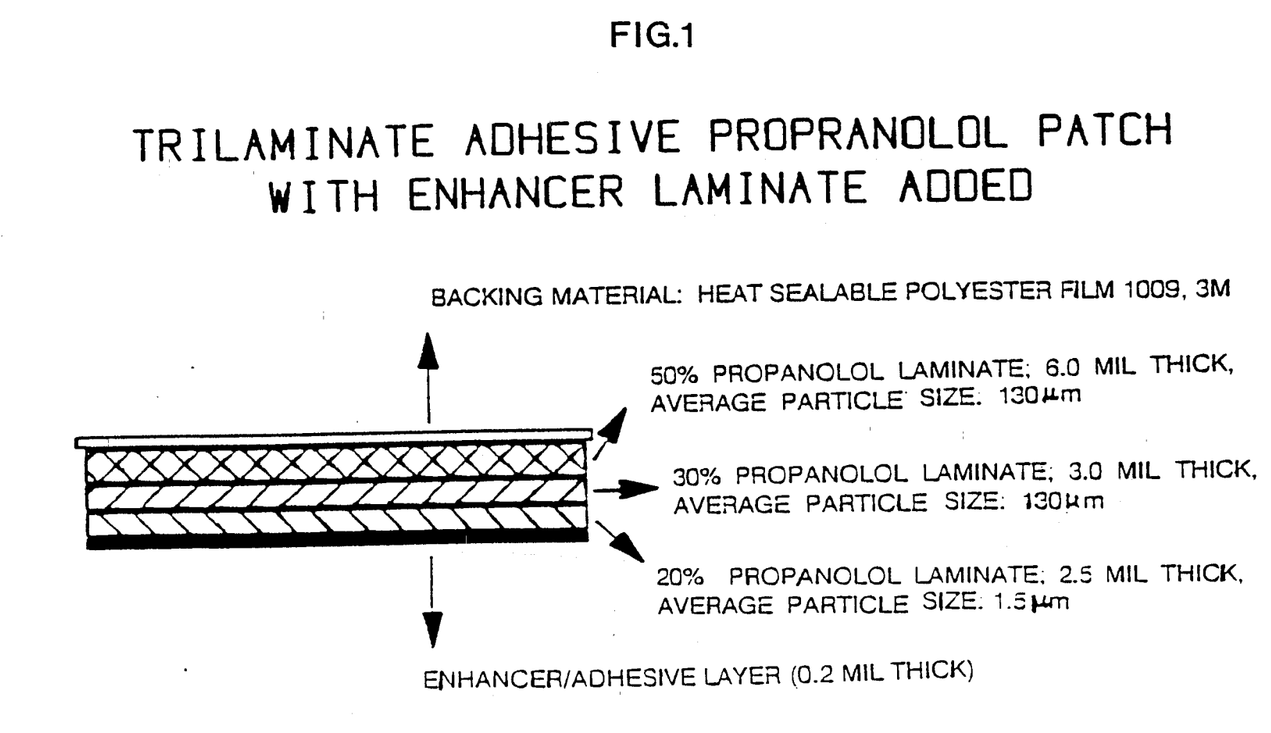
Figure 2:
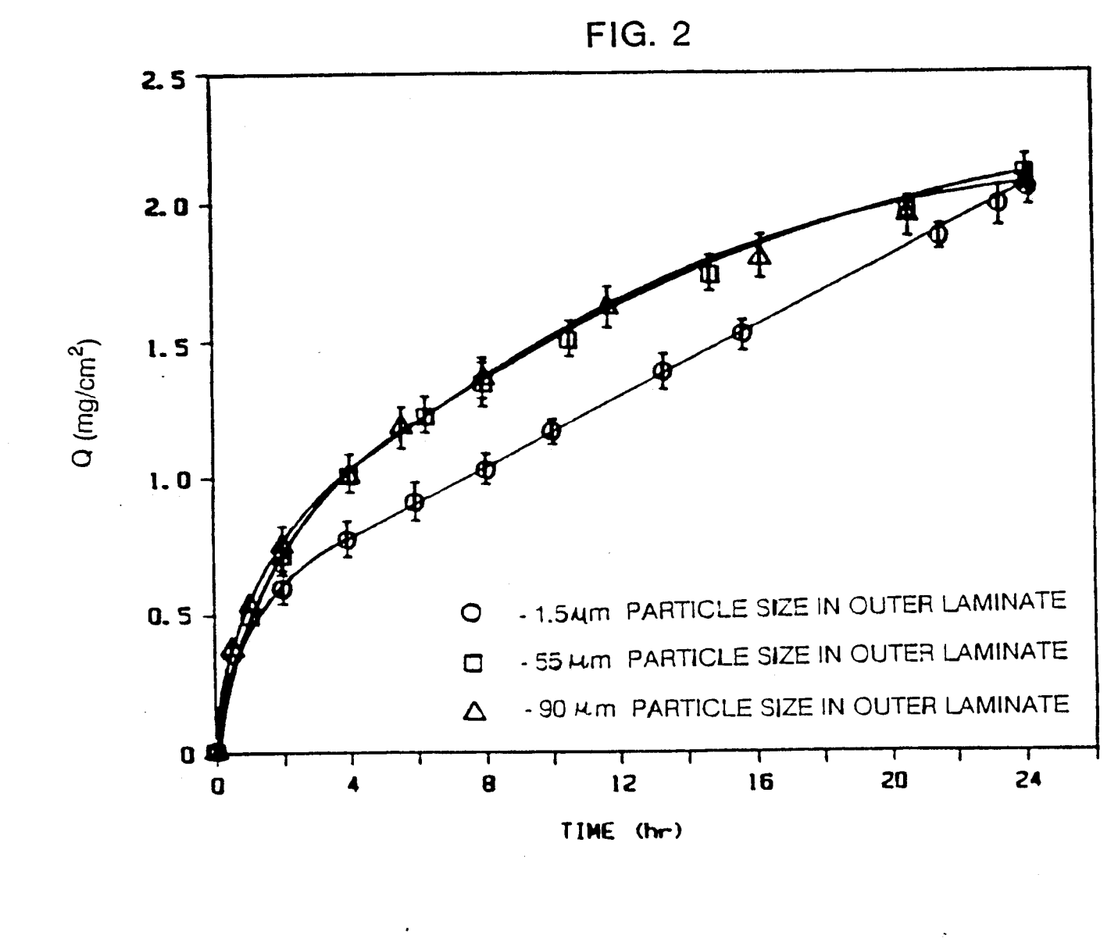
Figure 3:
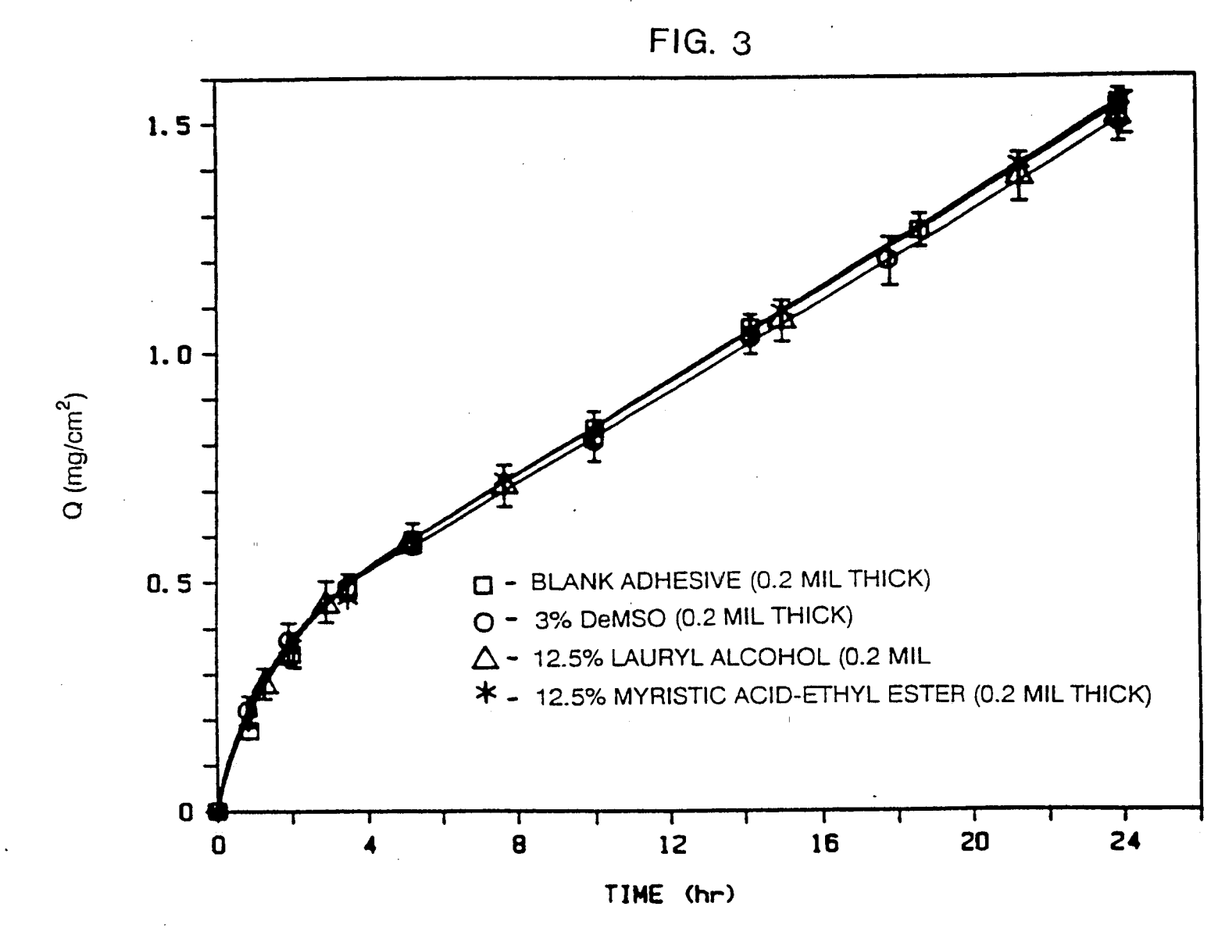
Figure 4:
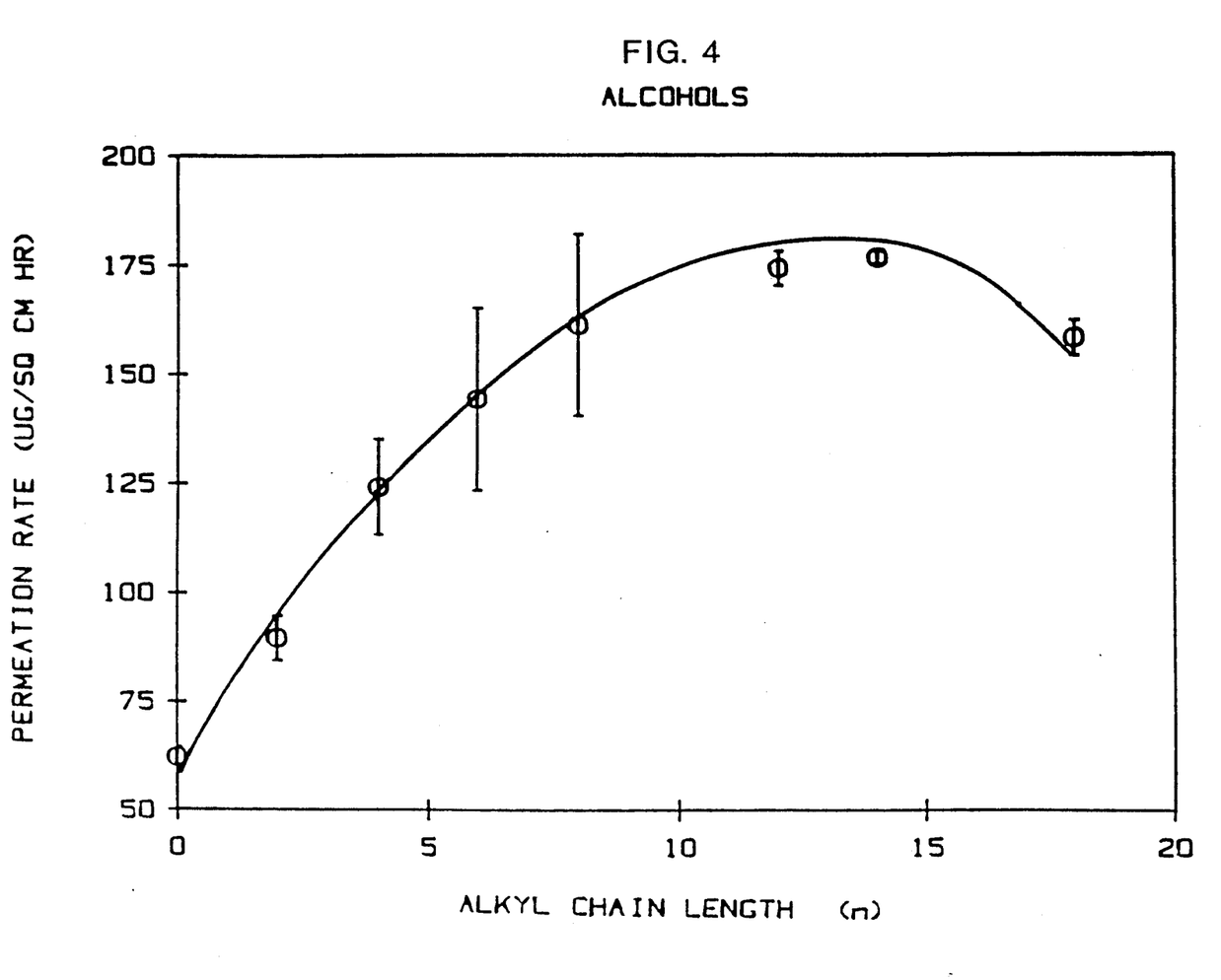
Figure 5:
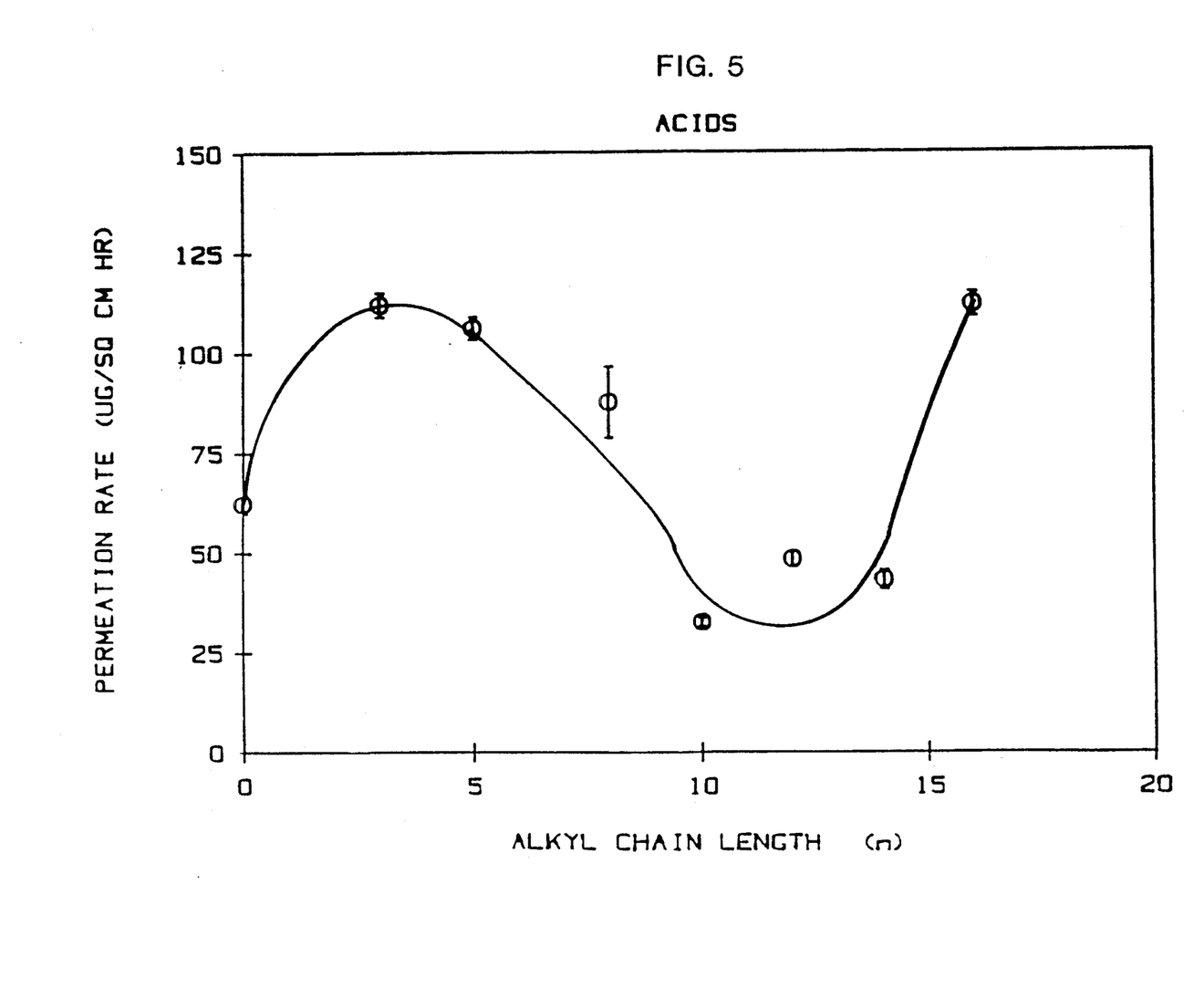
Figure 6:
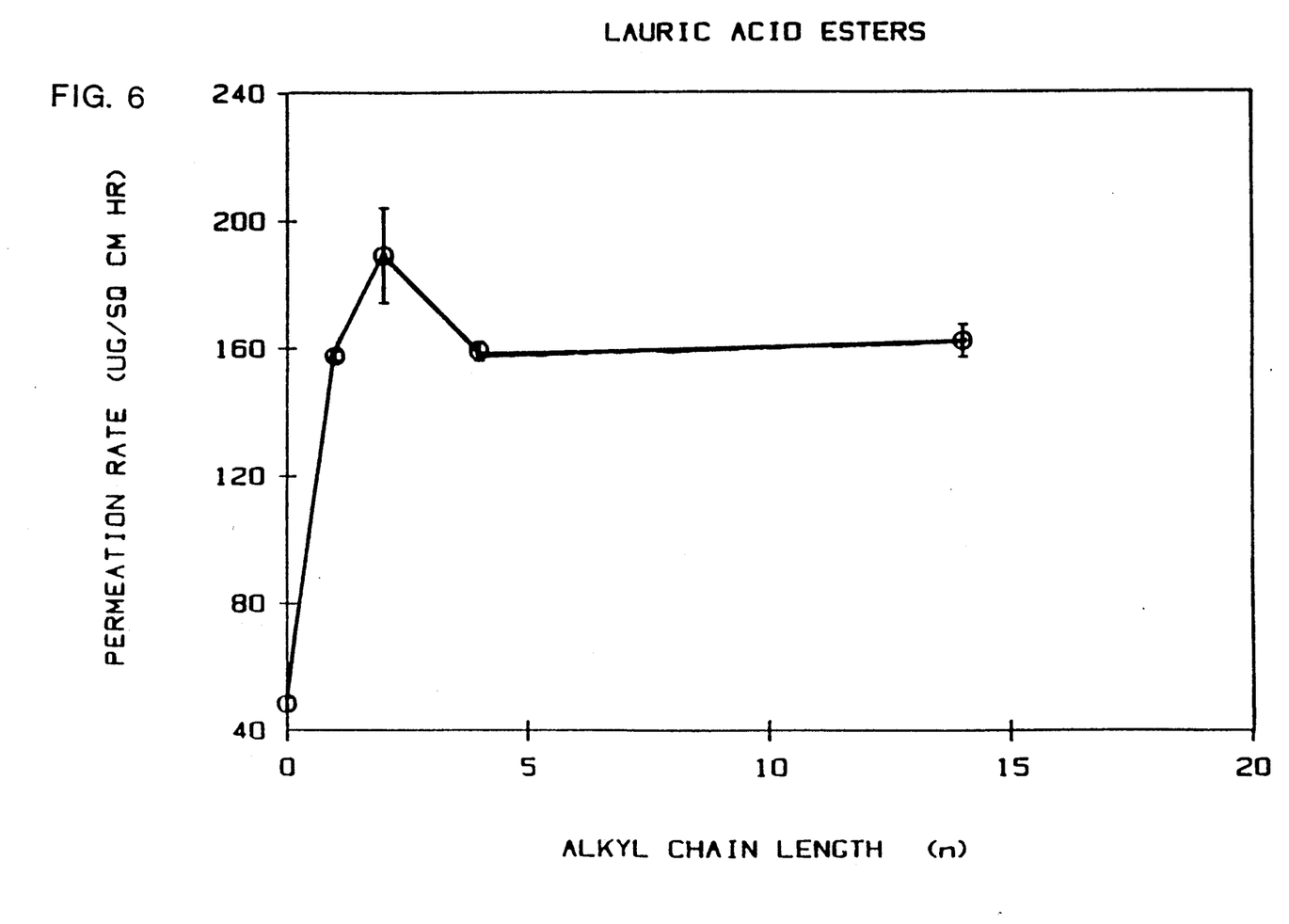
Figure 7:
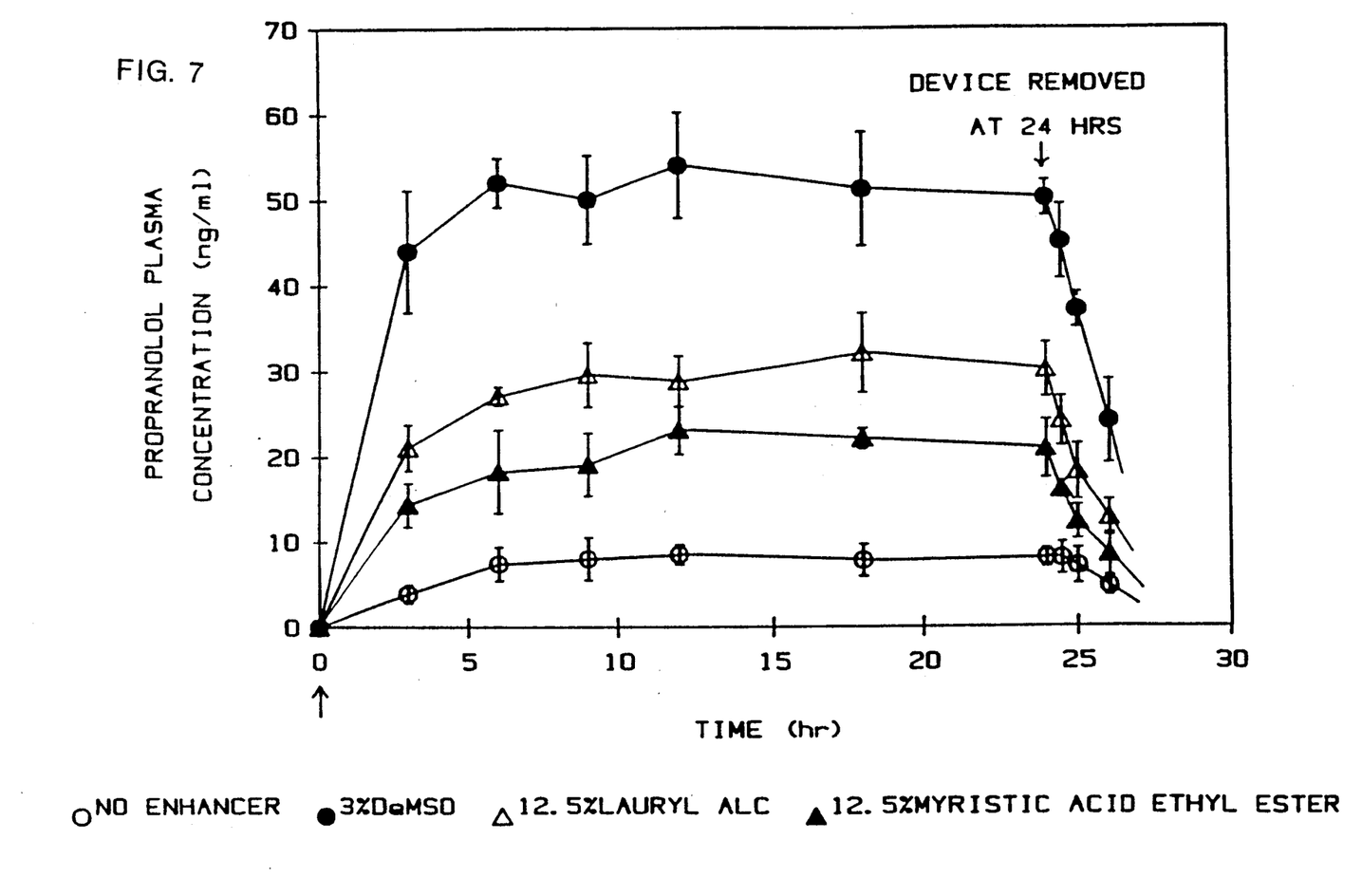

FIG. 5
ACIDS

FIG. 6

FIG. 7

TRANSDERMAL DOSAGE UNIT, SYSTEM AND PROCESS

CROSS-REFERENCE TO RELATED APPLICATION

This application is a continuation-in-part of U.S. application Ser. No. 06/705,194, filed Feb. 25, 1985 now abandoned.

TECHNICAL FIELD

This invention relates to novel transdermal dosage units for administering cardiovascular pharmaceuticals, whereby enhanced absorption is released and absorbed transdermally at essentially zero-order kinetics. It also relates to novel process of administration of cardiovascular pharmaceuticals by use of said dosage units.

BACKGROUND ART

A number of pharmaceuticals of various classes have been developed in quest to find effective treatment for cardiovascular problems. These pharmaceuticals fall into various classes including beta blockers, calcium channel blockers, antianginal agents, antihypertensives, antiarrhythmics, acetylcholine inhibitors, vasodilators, vasopressors and others such as are listed in Physicians' Desk Reference under cardiovascular preparations.

There is a need to improve the effeciency and effectiveness of treatment using these drugs.

There is further a specific need for improved dosage units for transdermal absorption dosage units which provide the pharmaceutical at essentially zero-order kinetics with the coincident advatages.

SUMMARY OF INVENTION

Provided by this invention is a transdermal dosage unit for transdermal adminstration of cardiovascular pharmaceuticals. In particular, this invention provides essentially zero-order kinetics in transdermal administration of crystalline forms of cardiovascular pharmaceuticals.

The transdermal dosage units provided are multiple layer or multilaminate system wherein the layers are formed using biocompatible adhesive polymer which are compatible with the pharmaceutical and permit release of the pharmaceutical for transdermal absorption.

The transdermal dosage units provided comprise a:

a) a backing layer which is substantially umpervious to the cardiovascular pharmaceutical crystals and any other components which contact the backing layer;

b) an inner pharmaceutical adhesive layer which adheres to the backing layer which has evenly dispersed therein relatively large crystals, for exanpke, desirably largely of the size of at least about 100 microns to about 200 microns or larger if suitable in the case of propanolol, the pharmaceutical is present in relatively large weight percentages, for example in the range of at least 40 percent, suitable about 50 percent or more, based on the weight of the final adhesive layer;

c) middle pharmaceutical adhesive layer which is adhered to the inner layer and which also has relatively large crystalline particles of the pharmacetical uniformly dispersed in the adhesive polymer, in a lesser weight percentage amount, for example in the range of about 20 to about 40 weight percent, suitably in a weight percent of about 30 weight percent based on the final adhesive layer weight;

d) outer pharmaceutical adhesive layer, which adhered to the middle adhesive pharmaceutical layer and which has uniformly dispersed therein pharmaceutical crystals of a relatively small size, for example largely in the size of about 0.5 to about 15 microns, suitably about 1.5 microns in the case of propanolol;

e) and an outer enhancer layer which contains an effective amount of one or more suitable skin permeation enhancer.

The pharmaceutical layers can have varied thickness in the micron range, for example, in the range of about 1 to about 10 microns has been found suitable for most applications. The outer enhancer layer usually has a lesser thickness, for example, a thickness in the range of about 0.1 to about 0.5 or about 1 micron has been found suitable for most applications.

The skin permeation enhancer is selected from those which are biocompatible, and compatible with the pharmaceutical. The amount of enhancer will vary depending upon the enhancer, the pharmaceutical, the adhesive used, and other factors. It has been found a weight amount of enhancer based upon the final adhesive layer weight of about 1 to about 15 is generally satisfactory, about 2-5 percent being suitable in the use of propanolol.

DETAILED DESCRIPTION OF THE INVENTION AND THE PREFERRED EMBODIMENTS

The backing layer can be made of any suitable material which is impermeable to the pharmaceuticals used of the polmer layer. The backing layer serves as a protective cover for the adhesive pharmaceutical layer and provides also a support function. The backing can be formed so that it is essentially the same size layer as the pharmaceutical adhesive layer or it can be of larger dimension so that it can extend beyond the side of the pharmaceutical adhesive layer or overlay the side or sides of the pharmaceutical adhesive layer and then can extend outwardly in a manner that the surface of the extension of the backing layer can be the base for adhesive.

The adhesive layers are suitably made using a silicone adhesive, such as a (polydimethylsiloxane-silicate resin) copolymer adhesive depicted by the following formula:

wherein Me is methyl and R is $-Si(CH_3)_3$ and x and y represent independent numbers of repeating units sufficient to provide the desired properties in the adhesive polymer and other polymer layers.

The outer adhesive layer is finally covered with a releasable protective film layer which is made from materials which are substantially impermeable to the hormones, the skin permeation enhancer, if used, and any other components of the dosages unit. The polymer materials and metal foil laminates used for the backing layer may also be used to make the protective layer, provided the layer is made strippable or releasable such as by applying conventional siliconizing or teflon coating. A suitable releasable material for use with silicone polymer adhesive DC-355 and X7-2970 is Scotchpak 1022 material sold by the 3M Company or Bio-Release Material by Dow Corning.

In making the pharmaceutical adhesive layers, silicone elastomers, such as (polydimethylsiloxanesilicate resin) copolymer, polyacrylic adhesive, such as sold under the designation Duro-Tak, of the formula described above, and other biocompatible adhesive polymers which provide a stable environment for the pharmaceutical and permit their release, can suitably be used.

The preparation of the pharmaceutical adhesive composition used in making the respective pharmaceutical adhesive layers is carried out following procedures within the skill of the art and illustrated in the Examples. Likewise, the formation of the respective layers to form the complete dosage unit is done following procedures generally known to those having skill in the art and illustrated in the Examples.

Cardiovascular pharmaceuticals include classes referred to above and can be selected for example, from the following:
Propranolol
Timolol
Atenolol
Oxprenolol
Metoprolol
Hydralazine
Prazosine
Verapamil
Nifedipine
Diltiazem
Dipyridamole
Disopyramide
Minoxidil

MULTILAMINATE TRANSDERMAL ADHESIVE DEVICE

(m-TAD)

EXAMPLE 1

SKIN-PERMEABILITY-ENHANCING MULTILAMINATE TRANSDERMAL ADHESIVE DEVICE

(SPE-m-TAD)

The SPE-m-TAD is a multilaminate adhesive device which can be used for the controlled transdermal administration of antihypertensive drugs at an enhanced rate. The device is composed of four basic laminates: an inner drug laminate composed of 50% drug in the adhesive (with an average drug particle size of 130 microns in the laminate), a middle drug laminate composed of 30% drug in the adhesive (with an average drug particle size of 130 microns in the laminate), an outer drug laminate composed of 20% drug in the adhesive (with an average drug particle size of 1.5 microns, acceptable range is from 1 to 12 microns) and an outer enhancer laminate which contains a skin permeability enhancer in the adhesive. An example of the system is shown on the attached pages.

In the following example, the following agents were used:
DRUG: Propranolol (in the free base form)
ENHANCER: Decyl Methyl Sulfoxide (DeMSO)
ADHESIVE: BIO/PSA X7-2920 (Dow Corning)

Method of Fabrication a) INNER DRUG LAMINATE (50% drug): The drug-adhesive dispersion for the inner drug laminate is fabricated by mixing the propranolol free base with methylene chloride (1:1) in a ground-glass stoppered flask, and then adding the adhesive solution (in an amount equal to 1 part adhesive, in this case, using an adhesive solution of 36% adhesive in volatile solvent (trichlorotrifluoroethane), this would be equal to 2.8 parts of the adhesive solution). The contents of the flask are then mixed on a rotating mixer at a 45° angle for 15 minutes. The resultant drug-adhesive dispersion has a composition of propranolol:adhesive: methylene chloride of 1:1:1 (by weight).

The drug-adhesive laminate can then be fabricated by a solvent casting method. The freshly made drug-adhesive dispersion is cast onto a polyester foil-coated backing material (1009, 3M Co.) by pulling the drug-adhesive dispersion across the backing material with a K-Bar, which is used to control the thickness of the laminate (in this case a 350 micron K-Bar was used). The laminates are cast in a stagnant environment to prevent bubble formation. After 30 minutes, the laminates are placed in a fume hood for 24 hours at room temperature to allow for the complete evaporation of the volatile solvents (methylene chloride and trichlorotrifluoroethane) from the laminate (complete evaporation was confirmed by Thermo-Gravimetric-Analysis). The final, dry laminate has a composition of propranolol:adhesive (1:1) with an average propranolol particle size of 150 microns, and is 4.0 mil thick.

b) MIDDLE DRUG LAMINATE (30% drug)

The middle drug laminate is fabricated in much the same fashion as the outer laminate. However, in this case, the drug-adhesive dispersion is composed of propranolol: adhesive:methylene chloride in a 1:2.3:1 ratio. The middle laminate is solvent cast onto a Teflon-coated polyester release liner (1022, 3M Co.) using a 150 micron K-Bar. The final, dry laminate is composed of propranolol:adhesive (1:3) with a propranolol particle size of 130 microns, and a thickness of 3.0 mil.

c) Outer Drug Laminate (20% drug)

The drug-adhesive dispersion is composed of propranolol:adhesive:methylene chloride in a 1:4:3 ratio. The drug-adhesive dispersion is solvent cast (as above) onto the Teflon-coated release liner with a 100 micron K-Bar, and dried. The final, dry laminate has a composition of propranolol:adhesive of 1:5, with a propranolol particle size of 1.5 microns, and a thickness of 2.5 mil.

d) Enhancer Laminate (3% Enhancer)

The enhancer-adhesive solution is composed of enhancer (decyl methyl sulfoxide, in this example) and adhesive (1:33). The enhancer-adhesive solution is solvent cast onto the Teflon-coated release liner using a 10 micron K-Bar. The final, dry laminate is composed of decyl methyl sulfoxide:adhesive (1:33), and is 0.2 mil thick.

e) Lamination Procedure for the Dried Laminates

The dried laminates are laminated in the following manner: The middle drug laminate (30% propranolol) is placed upon the inner drug laminate (50% propranolol), and the two laminates are pressed together under 4 kg of pressure using a stainless steel roller. Once they are laminated together, the release liner is peeled away from the middle drug laminate, and the outer drug laminate is placed upon it and laminated in the same fashion. Once the drug laminates have been combined, the enhancer laminate is laminated to the outer drug laminate in the same fashion. The final device is shown on the attached sheets.

Both in-vitro release and skin permeation studies can then be conducted by mounting the device (with or without skin) onto a Valia-Chien diffusion cell at 37° C. In-vivo studies can be conducted by placing the patch on the pinna (ear) of a rabbit and taking blood samples which can be analyzed for propranolol (results on the attached sheets).

EXAMPLE 2

SPE-m-TAD with Various Drug Release Rates

The release rate of drug from the SPE-m-TAD can be changed by the alteration of the drug load in the outer drug laminate. By manufacturing all of the other laminates in the same fashion, and decreasing the drug load in the outer drug laminate (keeping the particle size at 1.5 microns) the overall release of propranolol from the device can be reduced, while still maintaining zero-order release kinetics (results shown in attached table).

EXAMPLE 3

SPE-m-TAD Conatining Aliphatic Alcohols as Skin Permeability Enahcners

These devices can be fabricated in much the same way as in Example 1, with the exception that the enhnacer layer would contain an aliphatic alcohol instead of the decyl methyl sulfoxide.

In this case, the enhancer laminate would be fabricated by combining an aliphatic alcohol with adhesive in a 1.25:10 ratio. The enhancer laminate would then be solvent cast and laminated as in Example 1. The devices can then be evaluated in-vitro and in-vivo. (results shown on the attached sheets).

| EXAMPLE 2 | |
|---|---|
| PROPRANOLOL DRUG LOAD IN OUTER DRUG LAMINATE | RELEASE RATE OF PROPRANOLOL (ug cm$^{-2}$ hr$^{-1}$) |
| 20% | 59.1 |
| 7% | 52.2 |
| 5% | 49.9 |
| 3% | 48.1 |

FIG. A-1: Diagrammatic illustration of various major structural components in a propranolol-releasing transdermal multilaminate adhesive device (TMAD)

FIG. A-2: Device-controlled zero-order drug release kinetics was achieved by using only extremely small particle size (1.5 μm) of propranolol crystals in the outer laminate layer.

FIG. A-3: Incorporation of various skin permeation enhancers in the contact adhesive polymer coating on the drug-releasing surface did not affect the zero-order release profile of propranolol from TMAD.

FIG. A-4: Enhancement in the skin permeation rate of propranolol, delivered from TMAD, by alkyl alcohols. The rate of skin permeation increases as increasing the alkyl chain length of the alcohols and reaches the maximum level at $n = 12 \sim 14$.

FIG. A-5: Enhancement in the skin permeation rate of propranolol, delivered from TMAD, by alkanoic acids. The rate of skin permeation shows a sinoidal dependence on the alkyl chain length of the acids and with the maximum rates at $n = 3$ and 16.

FIG. A-6: Enhancement in the skin permeation rate of propranolol, delivered from TMAD, by the esters of Lauric Acid ($n = 12$). The rate of skin permeation increases first and then levels off as increasging the alkyl chain length of the esters and reaches the maximum level at $n = 2$.

FIG. A-7: The long-acting plasma concentration profiles of propranolol in the rabbits following 24-hr topical application of TMAD on the inner pinna ear. Incorporation of various skin permeation enhancers in the contact adhesive polymer coating on the drug-releasing surface has improved the systemic bioavailability, as shown by elevated constant plasma levels, of propranolol resulted from enhanced skin permeability.

What is claimed is

1. A transdermal cardiovascular pharmaceutical dosage unit wherein propanolol is said pharmaceutical, comprising:

a) a backing layer which is substantially impervious to said pharmaceutical;

b) an inner pharmaceutical adhesive first layer having the pharmaceutical dispersed uniformly in a relatively large and effective crystalline form in an amount of at least about 40 percent based on the final weight of said layer and having the predominant weight amount of said pharmaceutical present in a crystalline size of at least 100 microns;

c) a middle pharmaceutical adhesive second layer having the pharmaceutical dispersed uniformly in relatively large and effective crystalline form at a substantially lower concentration than used in said inner first layer in an amount of at least about 20 percent based on the final weight of said layer and having the predominant weight amount of said pharmaceutical present in a crystalline size of at least 100 microns;

d) an outer pharmaceutical adhesive third layer having the pharmaceutical dispersed uniformly in relatively small and effective crystalline form largely on a weight basis in the range of from about 1 to about 15 microns and in an effective amount up to at least about 40 percent based upon the final weight of said layer; and e) an outer adhesive fourth layer which contains an effective amount of one or more skin permeation enhancers; said adhesives of said layers being the same or different and being biocompatible, providing a stable environment for said pharmaceutical and permitting release of said pharmaceutical for said absorption; said dosage unit delivering said pharmaceutical for transdermal absorption at substantially zero-order kinetic rate.

2. A dosage unit in accordance with claim 1 in which the pharmaceutical is present in said fourth layer in an amount of about 20 percent.

* * * * *